United States Patent [19]

Berg et al.

[11] Patent Number: 5,131,985
[45] Date of Patent: Jul. 21, 1992

[54] SEPARATION OF CHLOROFORM FROM A LOWER ALCOHOL BY EXTRACTIVE DISTILLATION

[75] Inventors: Lloyd Berg, 1314 S. 3rd Ave., Bozeman, Mont. 59715; Zuyin Yang, Bozeman, Mont.

[73] Assignee: Lloyd Berg, Bozeman, Mont.

[21] Appl. No.: 709,615

[22] Filed: Jun. 3, 1991

[51] Int. Cl.$^5$ .................. B01D 3/40; C07C 17/38; C07C 29/84
[52] U.S. Cl. ............................ 203/57; 203/58; 203/60; 203/62; 203/63; 203/64; 568/913; 570/262
[58] Field of Search ............... 203/60, 63, 62, 58, 203/57, 64, DIG. 23; 568/913, 918; 570/262

[56] References Cited

U.S. PATENT DOCUMENTS 893,784 7/1908 Chute .................. 570/262

FOREIGN PATENT DOCUMENTS 142183 6/1980 German Democratic Rep. ... 203/64
197544 7/1967 U.S.S.R. ...................... 570/262

*Primary Examiner*—Wilbur Bascomb, Jr.

[57] ABSTRACT

Chloroform cannot be completely separated from methanol, ethanol or isopropanol by conventional distillation or rectification because of the minimum boiling azeotrope between chloroform and the alcohols. Chloroform can be readily separated from methanol, ethanol or isopropanol by extractive distillation. Typical effective agents are: for methanol, isopropanol or 4-methyl-2-pentanone; for ethanol, n-butanol or isobutyl acetate; for isopropanol, butyl acetate or ethylene glycol ethyl ether.

5 Claims, No Drawings

SEPARATION OF CHLOROFORM FROM A LOWER ALCOHOL BY EXTRACTIVE DISTILLATION

FIELD OF THE INVENTION

This invention relates to a method for separating chloroform from methanol, ethanol or isopropanol using certain organic compounds as the agent in extractive distillation.

DESCRIPTION OF PRIOR ART

Extractive distillation is the method of separating close boiling compounds or azeotropes by carrying out the distillation in a multi-plate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally from an azeotrope, the proper agents will cause them to boil separately during the extractive distillation and this make possible a separation in a rectification column that cannot be done at all when no agent is present. The extractive agent should boil higher than any of the close boiling liquids being separated and not from minimum azeotropes with them. Usually the extractive agent is introduced a few plates from the top of the column to insure that none of the extractive agent is carried over with the lower boiling component. This usually requires that the extractive agent boil twenty Celcius degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

Chloroform, B.P.=61° C. forms a minimum boiling azeotrope with methanol, B.P.=64.6° C. at 53° C. containing 87% chloroform. Chloroform forms a minimum boiling azeotrope with ethanol, B.P.=78° C. containing 93% chloroform. Chloroform forms a minimum boiling azeotrope with isopropanol, B.P.=82° C. containing 95% chloroform. The chloroform-alcohol azeotropes are impossible to separate by distillation because the relative volatility of an azeotrope is 1.0. Extractive distillation would be an attractive method of effecting the separation of chloroform from these alcohols if agents can be found that (1) will enhance the relative volatility between chloroform and these alcohols and (2) are easy to recover, that is, form no azeotrope with chloroform, methanol, ethanol or isopropanol and boil sufficiently above these four to make separation by rectification possible with only a few theoretical plates.

Extractive distillation typically requires the addition of an equal amount to twice as much extractive agent as the chloroform-alcohol on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is desirable that the extractive agent be miscible with chloroform-alcohols otherwise it will form a two-phase azeotrope with the alcohols in the recovery column and some other method of separation will have to be employed.

TABLE 1

Effect of Relative Volatility on the Separation of Chloroform from Alcohols at 99% Purity by Extractive Distillation

| Relative Volatility | Theoretical Plates | Actual Plates 75% Efficiency | Actual Plates 75% Eff., Min Reflux |
|---|---|---|---|
| 1.2 | 50 | 67 | 87 |
| 1.3 | 35 | 47 | 61 |
| 1.4 | 27 | 36 | 47 |
| 1.5 | 23 | 31 | 40 |
| 1.6 | 20 | 27 | 35 |
| 1.7 | 17 | 23 | 29 |

The advantage of employing an effective extractive distillation agent for this separation is shown in Table 1. Ordinary rectification cannot completely separate chloroform from these alcohols because of the minimum azeotrope. When extractive distillation is employed with an agent that converts the relative volatility to 1.5, only 31 actual plates are required.

OBJECTIVE OF THE INVENTION

The objects of this invention are to provide a process or method of extractive distillation that will enhance the relative volatility of chloroform to methanol, ethanol or isopropanol in their separation in a rectification column. It is a further object of this invention to identify organic compounds that are stable, can be separated from the chloroform or alcohols by rectification with relatively few paltes and can be recycled to the extractive distillation column with little decomposition.

SUMMARY OF THE INVENTION

The objects of this invention are provided by a process for the separation of chloroform from methanol, ethanol or isopropanol which entails the use of certain organic compounds as the agent in extractive distillation.

DETAILED DESCRIPTION OF THE INVENTION

We have discovered that certain organic compounds will effectively increase the relative volatility between chloroform and methanol, ethanol or isopropanol by rectification when employed as the agent in extractive distillation. The data in Tables 2, 3, 5, 7 and 8 was obtained in a vapor-liquid equilibrium still. In every case, the starting mixture was the chloroform-methanol, ethanol or isopropanol azeotrope. The relative volatilities are listed for each of the agents. Table 2 lists the agents that we have found to be effective extractive distillation agents to separate chloroform from methanol. The compounds which are effective are n-propanol, isopropanol, 2-butanol, t-butanol, methyl acetate, ethyl acetate, n-propyl acetate, isobutyl acetate, isoamyl acetate, n-butyl acetate, dioxane, vinyl n-butyl ether, vinyl isobutyl ether, propylene glycol methyl ether, 2-pentanone, diisobutyl ketone, 3-pentanone, 3-hexanone, 2-hexanone, 2-heptanone, 4-methyl-2-pentanone, methyl isobutyl ketone, 3-heptanone and triethyl amine. The starred compounds bring chloroform out as overhead, the others bring methanol out as overhead. Table 3 lists a number of compounds that proved to be ineffective as extractive distillation agents in the separation of methanol from chloroform. Two of the agents whose relative volatility had been determined in the vapor-liquid equilibrium still were then evaluated in a glass perforated plate rectification column possessing 7.3 theoretical plates and the results listed in Table 4. 4-Methyl-2-pentanone brought methanol out as overhead and gave a relative volatility of 1.64 after two hours of continuous operation. Isopropanol brought chloroform out as overhead and gave a relative volatility of of 1.75 after two hours. Table 5 lists the agents that we have found to be effective extractive distillation agents to separate chloroform from ethanol. The compounds which are effective are ethyl acetate, isopropyl acetate, n-propyl acetate, isobutyl acetate, n-butyl acetate, isoamyl acetate, n-amyl acetate, 3-pentanone, methyl isobutyl ketone, methyl isopropyl ketone, 4-methyl-2-pentanone, 2-pentanone, 3,3-dimethyl-2-butanone, 3-methyl-2-butanone, dimethyl carbonate, methyl propionate, 2,2-methoxyethoxyethyl ether, n-butyl ether, 5-methyl-2-hexanone, ethyl valerate, n-butanol, isobutanol, 2-butanol, t-amyl alcohol, isoamyl alcohol, hexyl alcohol, and ethylene glycol methyl ether. The starred compounds bring chloroform out as overhead, the others bring ethanol out as overhead.

TABLE 2

| Effective Agents For Separating Methanol From Chloroform | |
|---|---|
| Compounds | Relative Volatility |
| n-Butyl acetate | 2.0 |
| n-Amyl acetate | 2.1 |
| Isobutyl acetate | 1.7 |
| n-Propyl acetate | 1.25 |
| Iso-Propyl acetate | 1.2 |
| Ethyl acetate | 1.5 |
| 2,2-Dimethoxypropane | 1.75 |
| Mesityl oxide | 1.55 |
| 2-Hexanone | 1.65 |
| 3-Pentanone | 1.5 |
| 4-Methyl-2-pentanone | 1.65 |
| Diisobutyl ketone | 1.35 |
| Vinyl acetate | 1.2 |
| Methyl vinyl acetate | 1.4 |
| Dioxane | 1.45 |
| 3-Methyl-2-butanone | 1.4 |
| Methyl isopropyl ketone | 1.5 |
| Methyl isobutyl ketone | 1.4 |
| 5-Methyl-2-hexanone | 1.4 |
| 2-Heptanone | 1.95 |
| 3-Methyl-1-butanol | 2.0* |
| Propylene glycol methyl ether | 1.35* |
| n-Butanol | 1.85* |
| Isobutanol | 1.9* |
| 2-Butanol | 1.5* |
| t-Butanol | 1.55* |
| n-Propanol | 1.2* |
| Isopropanol | 2.0* |
| t-Amyl alcohol | 1.3* |
| n-Amyl alcohol | 1.7* |
| Nitromethane | 1.6 |
| Nitroethane | 1.25 |
| 1-Nitropropane | 1.3 |

TABLE 2-continued

| Effective Agents For Separating Methanol From Chloroform | |
|---|---|
| Compounds | Relative Volatility |
| 2-Nitropropane | 1.3 |

*Brings Chloroform Out As Overhead

TABLE 3

| Ineffective Agents, Methanol From Chloroform | |
|---|---|
| Methyl isoamyl ketone | 3,3-Dimethyl-2-butanone |
| 2-Octanone | Ethylene glycol ethyl ether acetate |
| Diacetone alcohol | 2,6-Dimethyl-4-heptanone |
| 3-Heptanone | 2-Methoxyethyl acetate |

TABLE 4

Data From Runs Made In Rectification Column- Methanol From Chloroform

| Agent | Column | Time hrs. | Weight % Methanol | Weight % Chloroform | Relative Volatility |
|---|---|---|---|---|---|
| 4-Methyl-2-pentanone | Overhead | 1 | 80.7 | 19.3 | 1.47 |
| | Bottoms | | 20.3 | 79.7 | |
| 4-Methyl-2-pentanone | Overhead | 2 | 90 | 10 | 1.64 |
| | Bottoms | | 21.5 | 88.5 | |
| isopropanol | Overhead | 1 | 4.9 | 95.1 | 1.45* |
| | Bottoms | | 43.5 | 56.5 | |
| isopropanol | Overhead | 2 | 1.9 | 98.1 | 1.75* |
| | Bottoms | | 53.2 | 46.8 | |

*Brings Chloroform Out As Overhead

Two of the agents whose relative volatility had been determined in the vapor-liquid equilibrium still were then evaluated in a glass perforated plate rectification column possessing 7.3 theoretical plates and the results listed in Table 6. Isobutyl acetate brought ethanol out as overhead and gave a relative volatility of 1.60 after two hours of continuous operation. n-Butanol brought chloroform out as overhead and gave a relative volatility of 1.28 after two hours of operation.

Table 7 lists the agents that we have found to be effective extractive distillation agents to separate chloroform from isopropanol. The compounds which are effective are n-butyl acetate, ethyl acetate, 3-pentanone, dimethyl carbonate, 1-methoxy-2-propanol, mesityl oxide, 4-methyl-2-pentanone, ethylene glycol methyl ether, ethylene glycol ethyl ether, 2-methoxyethyl ether, dibutyl ether, ethyl valerate, 1-nitropropane, 2-nitropropane, 3-methyl-2-butanone, methyl vinyl acetate, 2,4-pentanedione, propyl butyrate, propylene glycol methyl ether, 3-hexanone, ethyl butyrate, 2-pentanone, methyl isoamyl ketone, ethyl isovalerate and ethyl acetoacetate. The starred compounds bring chloroform out as overhead, the others bring isopropanol out as overhead. Table 8 lists a number of compounds that proved to be ineffective as extractive distillation agents in the separation of isopropanol from chloroform. Two of the agents whose relative volatility had been determined in the vapor-liquid equilibrium still were then evaluated in the 7.3 theoretical plate glass perforated plate column and the results listed in Table 9. 4-Methyl-2-pentanone brought out isopropanol as overhead and gave a relative volatility of 1.43 after two hours. Ethylene glycol brought out chloroform as overhead and gave a relative volatility of 1.34 after two hours.

TABLE 5

Effective Agents For Separating Ethanol From Chloroform

| Compounds | Relative Volatility |
|---|---|
| Ethyl acetate | 1.2 |
| Isopropyl acetate | 2.0 |
| n-Propyl acetate | 1.35 |
| Isobutyl acetate | 1.6 |
| n-Butyl acetate | 1.8 |
| Isoamyl acetate | 2.1 |
| n-Amyl acetate | 2.3 |
| 3-Pentanone | 2.3 |
| Methyl isobutyl ketone | 1.4 |
| Methyl isopropyl ketone | 1.45 |
| 4-Methyl-2-pentanone | 1.55 |
| 2-Pentanone | 1.6 |
| 3,3-Dimethyl-2-butanone | 1.9 |
| 3-Methyl-2-butanone | 1.65 |
| Dimethyl carbonate | 1.45 |
| Methyl propionate | 2.7 |
| 2,2-Methoxyethoxyethyl ether | 2.1 |
| n-Butyl ether | 1.9 |
| 5-Methyl-2-hexanone | 1.9 |
| Ethyl valerate | 2.3 |
| n-Butanol | 1.3* |
| Isobutanol | 1.25* |
| 2-Butanol | 2.6* |
| t-Amyl alcohol | 2.0* |
| Isoamyl alcohol | 2.1* |
| Hexyl alcohol | 1.6* |
| Ethylene glycol methyl ether | 2.0* |

*Brings Chloroform Out As Overhead

TABLE 6

Data From Runs Made In Rectification Column- Ethanol From Chloroform

| Agent | Column | Time hrs. | Weight % Ethanol | Weight % Chloroform | Relative Volatility |
|---|---|---|---|---|---|
| Isobutyl acetate | Overhead | 1 | 47.9 | 52.1 | 1.32 |
| | Bottoms | | 10.7 | 89.3 | |
| Isobutyl acetate | Overhead | 2 | 80.6 | 19.4 | 1.60 |
| | Bottoms | | 11.5 | 88.5 | |
| n-Butanol* | Overhead | 1 | 2.5 | 97.5 | 1.27 |
| | Bottoms | | 12.7 | 87.3 | |
| n-Butanol* | Overhead | 2 | 1.5 | 98.5 | 1.28 |
| | Bottoms | | 8.4 | 91.6 | |

*Brings Chloroform Out As Overhead

TABLE 7

Effective Agents For Separating Isopropanol From Chloroform

| Compounds | Relative Volatility |
|---|---|
| n-Butyl acetate | 1.35 |
| Ethyl acetate | 1.9* |
| 3-Pentanone | 1.6* |
| Dimethyl carbonate | 1.7 |
| 1-Methoxy-2-propanol | 1.7* |
| Mesityl oxide | 1.2 |
| 4-Methyl-2-pentanone | 1.4 |
| Ethylene glycol methyl ether | 1.8 |
| Ethylene glycol ethyl ether | 1.35* |
| 2-Methoxyethyl ether | 1.65 |
| Dibutyl ether | 1.2 |
| Ethyl valerate | 1.3 |
| 1-Nitropropane | 1.3 |
| 2-Nitropropane | 1.2 |
| 3-Methyl-2-butanone | 1.45 |
| Methyl vinyl acetate | 1.45 |
| 2,4-Pentanedione | 1.2 |
| Propyl butyrate | 1.2* |
| Propylene glycol methyl ether | 1.3 |
| 3-Hexanone | 2.1 |
| Ethyl butyrate | 1.8 |
| 2-Pentanone | 1.4* |
| Methyl isoamyl ketone | 1.6 |
| Ethyl isovalerate | 1.5 |

TABLE 7-continued

Effective Agents For Separating Isopropanol From Chloroform

| Compounds | Relative Volatility |
|---|---|
| Ethyl acetoacetate | 1.6 |

*Brings chloroform out as overhead

TABLE 8

Ineffective Agents For Separating Isopropanol From Chloroform

| | |
|---|---|
| Isobutyl acetate | n-Propyl acetate |
| n-Amyl acetate | Methyl isobutyl ketone |
| 2-Pentanone | Dioxane |
| Nitromethane | 3,3-Dimethyl-2-butanone |
| Nitroethane | 5-Methyl-2-hexanone |
| Propoxypropanol | Ethyl propionate |
| 3-Heptanone | Isobutyl butyrate |

TABLE 9

Data From Runs Made In Rectification Column- Isopropanol From Chloroform

| Agent | Column | Time hrs. | Weight % Isopropanol | Weight % Chloroform | Relative Volatility |
|---|---|---|---|---|---|
| 4-Methyl-2-pentanone | Overhead | 1 | 35 | 65 | 1.38 |
| | Bottoms | | 4.8 | 95.2 | |
| 4-Methyl-2-pentanone | Overhead | 2 | 41.6 | 58.4 | 1.43 |
| | Bottoms | | 5.1 | 94.9 | |
| Ethylene glycol ethyl ether* | Overhead | 1 | 2.3 | 97.7 | 1.23 |
| | Bottoms | | 9.8 | 90.2 | |
| Ethylene glycol ethyl ether* | Overhead | 2 | 2.5 | 97.5 | 1.34 |
| | Bottoms | | 18 | 82 | |

*Brings chloroform out as overhead

THE USEFULNESS OF THE INVENTION

The usefulness or utility of this invention can be demonstrated by referring to the data presented in Tables 2 to 9. All of the successful agents show that chloroform can be separated from methanol, ethanol or isopropanol by means of extractive distillation in a rectification column and that the ease of separation as measured by relative volatility is considerable.

WORKING EXAMPLES

Example 1

Sixty grams of the chloroform-methanol azeotrope and 30 grams of 4-methyl-2-pentanone were charged to a vapor-liquid equilibrium still and refluxed for three hours. Analysis indicated a vapor composition of 51% methanol, 49% chloroform; a liquid composition of 39% methanol, 61% chloroform which is a relative volatility of methanol to chloroform of 1.65.

Example 2

Sixty grams of the chloroform-methanol azeotrope and 30 grams of isopropanol were charged to the vapor-liquid equilibrium still and refluxed for five hours. Analysis indicated a vapor composition of 71.9% chloroform, 28.1% methanol; a liquid composition of 55.5% chloroform, 44.5% methanol which is a relative volatility of chloroform to methanol of 2.0.

Example 3

A solution comprising 174 grams of chloroform and 26 grams of methanol was placed in the stillpot of a 7.3 theoretical plate rectification column. When refluxing began, an extractive agent comprising isopropanol was pumped into the column at a rate of 15 ml/min. The temperature of the extractive agent as it entered the column was 85° C. After establishing the feed rate of the extractive agent, the heat input to the chloroform-methanol in the stillpot was adjusted to give a total reflux rate of 40 ml/min. After two hours of operation, the overhead and bottoms samples of approximately two ml. were collected and analysed by gas chromatography. The overhead analysis was 98.1% chloroform, 1.9% methanol and the bottoms analysis was 46.8% chloroform, 53.2% methanol. This gives an average relative volatility of 1.75 for each theoretical plate. This data is presented in Table 4.

Example 4

Sixty grams of the chloroform-ethanol azeotrope and 30 grams of isobutyl acetate were charged to a vapor-liquid equilibrium still and refluxed for 12 hours. Analysis indicated a vapor composition of 16.7% ethanol, 83.3% chloroform; a liquid composition of 10.1% 10.1% ethanol, 89.9% chloroform which is a relative volatility of ethanol to chloroform of 1.75.

Example 5

Sixty grams of the chloroform-ethanol azeotrope and 30 grams of n-butanol were charged to the vapor-liquid equilibrium still and refluxed for 12 hours. Analysis indicated a vapor composition of 85% chloroform, 15% ethanol; a liquid composition of 81.9% chloroform, 18.1% ethanol which is a relative volatility of chloroform to ethanol of 1.25.

Example 6

A solution comprising 279 grams of chloroform and 21 grams of ethanol was placed in the stillpot of a 7.3 theoretical plate rectification column. When refluxing began, an extractive agent comprising n-butanol was pumped into the column at a rate of 15 ml/min. The temperature of the extractive agent as it entered the column was 85° C. After establishing the feed rate of the extractive agent, the heat input to the chloroform-ethanol in the stillpot was adjusted to give a total reflux rate of 40 ml/min. After hours of operation, the overhead and bottoms samples of approximately two ml. were collected and analysed by gas chromatography. The overhead analysis was 98.5% chloroform, 1.5% ethanol and the bottoms analysis was 91.6% chloroform, 8.4% ethanol. This gives an average relative volatility of 1.28 for each theoretical plate. This data is presented in Table 6.

Example 7

Sixty grams of the chloroform-isopropanol azeotrope and 30 grams of 4-methyl-2-pentanone were charged to a vapor-liquid equilibrium still and refluxed for four hours. Analysis indicated a vapor composition of 13.8% isopropanol, 86.2% chloroform, a liquid composition of 9.9% isopropanol, 90.1% chloroform which is a relative volatility of isopropanol to chloroform of 1.4.

Example 8

Sixty grams of the chloroform-isopropanol azeotrope and 30 grams of ethylene glycol ethyl ether were charged to the vapor-liquid equilibrium still and refluxed for four hours. Analysis indicated a vapor composition of 89.9% chloroform, 10.1% isopropanol; a liquid composition of 13% chloroform, 87% isopropanol which is a relative volatility of chloroform to isopropanol of 1.35.

Exmaple 9

A solution comprising 279 grams of chloroform and 21 grams of isopropanol was placed in the stillpot of a 7.3 theoretical plate rectification column. When refluxing began, an extractive agent comprising 4-methyl-2-pentanone was pumped into the column at a rate of 15 ml/min. The temperature of the extractive agent as it entered the column was 85° C. After establishing the feed rate of the extractive agent, the heat input to the chloroform-isopropanol in the stillpot was adjusted to give a total reflux rate of 40 ml/min. After two hours of operation, the overhead and bottoms samples of approximately two ml. were collected and analysed by gas chromatography. The overhead analysis was 58.4% chloroform, 41.6% isopropanol and the bottoms analysis was 94.9% chloroform, 5.1% isopropanol. This gives an average relative volatility of 1.43 for each theoretical plate. This data is presented in Table 9.

We claim:

1. A method for recovering chloroform from a mixture of chloroform and methanol which comprises distilling a mixture of chloroform and methanol in the presence of about one part of an extractive agent per part of chloroform-methanol mixture, recovering methanol as overhead product and obtaining the chloroform and the extractive agent from the stillpot, wherein said extractive agent consists of one material selected from the group consisting of n-butyl acetate, n-amyl acetate, isobutyl acetate, n-propyl acetate, isopropyl acetate, ethyl acetate, 2,2-dimethoxypropane, mesityl oxide, 2-hexanone, 3-pentanone, 4-methyl-2-pentanone, diisobutyl ketone, vinyl acetate, methyl vinyl acetate, dioxane, 3-methyl-2-butanone, methyl isopropyl ketone, methyl isobutyl ketone, 5-methyl-2-hexanone, 2-heptanone, nitromethane, nitroethane, 1-nitropropane and 2-nitropropane.

2. A method for recovering chloroform from a mixture of chloroform and methanol which comprises distilling a mixture of chloroform and methanol in the presence of about one part of an extractive agent per part of chloroform-methanol mixture, recovering methanol as overhead product and obtaining the chloroform and the extractive agent from the stillpot, wherein said extractive agent consists of one material selected from the group consisting of ethyl acetate, isopropyl acetate, n-propyl acetate, isobutyl acetate, n-butyl acetate, isoamyl acetate, n-amyl acetate, 3-pentanone, methyl isobutyl ketone, methyl isopropyl ketone, 4-methyl-2-pentanone, 2-pentanone, 3,3-dimethyl-2-butanone, 3-methyl-2-butanone, dimethyl carbonate, methyl propionate, 2,2-methoxyethoxyethyl ether, n-butyl ether, 5-methyl-2-hexanone and ethyl valerate.

3. A method for recovering chloroform from a mixture of chloroform and methanol which comprises distilling a mixture of chloroform and methanol in the presence of about one part of an extractive agent per part of chloroform-methanol mixture, recovering chloroform as overhead product and obtaining the methanol and the extractive agent from the stillpot, wherein said extractive agent consists of one material selected from the group consisting of n-butanol, isobutanol, 2-butanol, t-amyl alcohol, isoamyl alcohol, hexyl alcohol and ethylene glycol methyl ether.

4. A method for recovering chloroform from a mixture of chloroform and isopropanol which comprises distilling a mixture of chloroform and isopropanol in the presence of about one part of an extractive agent per part of chloroform-isopropanol mixture, recovering isopropanol overhead product and obtaining the chloroform and the extractive agent from the stillpot, wherein said extractive agent consists of one material selected from the group consisting of n-butyl acetate, dimethyl carbonate, mesityl oxide, 4-methyl-2-pentanone, ethylene glycol methyl ether, 2-methoxyethyl ether, dibutyl ether, ethyl valerate, 1-nitropropane, 2-nitropropane, 3-methyl-2-butanone, methyl vinyl acetate, 2,4-pentanedione, propylene glycol methyl ether, 3-hexanone, ethyl butyrate, methyl isoamyl ketone, ethyl isovalerate and ethyl acetoacetate.

5. A method for recovering chloroform from a mixture of chloroform and isopropanol which comprises distilling a mixture of chloroform and isopropanol in the presence of about one part of an extractive agent per part of chloroform-isopropanol mixture, recovering chloroform as overhead product and obtaining the isopropanol and the extractive agent from the stillpot, wherein said extractive agent consists of one material selected from the group consisting of ethyl acetate, 3-pentanone, 1-methoxy-2-propanol, ethylene glycol ethyl ether, propyl butyrate and 2-pentanone.

* * * * *